US010088657B2

(12) United States Patent
Dodt et al.

(10) Patent No.: US 10,088,657 B2
(45) Date of Patent: Oct. 2, 2018

(54) LIGHT SHEET MICROSCOPY USING MESO-OPTICAL ELEMENTS

(71) Applicants: Hans-Ulrich Dodt, München (DE); Saiedeh Saghafi, Vienna (AT)

(72) Inventors: Hans-Ulrich Dodt, München (DE); Saiedeh Saghafi, Vienna (AT)

(*) Notice: Subject to any disclaimer, the term of this patent is extended or adjusted under 35 U.S.C. 154(b) by 0 days.

(21) Appl. No.: 15/317,281

(22) PCT Filed: Jun. 10, 2015

(86) PCT No.: PCT/EP2015/062887
§ 371 (c)(1),
(2) Date: Dec. 8, 2016

(87) PCT Pub. No.: WO2015/189240
PCT Pub. Date: Dec. 17, 2015

(65) Prior Publication Data
US 2017/0115475 A1 Apr. 27, 2017

(30) Foreign Application Priority Data
Jun. 11, 2014 (DE) .................. 10 2014 008 811

(51) Int. Cl.
| G02B 21/08 | (2006.01) |
| G02B 5/00 | (2006.01) |
| G02B 27/42 | (2006.01) |
| G02B 27/09 | (2006.01) |
| G02B 21/00 | (2006.01) |
| G01N 21/64 | (2006.01) |

(52) U.S. Cl.
CPC ......... *G02B 21/08* (2013.01); *G01N 21/6458* (2013.01); *G02B 5/001* (2013.01); *G02B 21/0048* (2013.01); *G02B 21/0076* (2013.01); *G02B 27/0927* (2013.01); *G02B 27/425* (2013.01)

(58) Field of Classification Search
CPC .... G02B 21/06; G02B 5/001; G02B 21/0048; G02B 21/08; G02B 27/0927; G02B 21/0076; G02B 27/425; G01N 21/6458
See application file for complete search history.

(56) References Cited

U.S. PATENT DOCUMENTS

| 1,988,946 A | 1/1935 | Hauser et al. |
| 5,583,342 A | 12/1996 | Ichie |

(Continued)

FOREIGN PATENT DOCUMENTS

| CA | 2 668 095 A2 | 12/2010 |
| DE | 10 2009 008 646 A1 | 8/2010 |

(Continued)

OTHER PUBLICATIONS

English Translation of the International Preliminary Report on Patentability from Corresponding Application No. PCT/EP2015/062887; dated Aug. 5, 2015.

(Continued)

*Primary Examiner* — David Porta
*Assistant Examiner* — Faye Boosalis
(74) *Attorney, Agent, or Firm* — Pearne & Gordon LLP

(57) ABSTRACT

The present application relates to devices and methods for generating light sheets and thin light beams with high Rayleigh lengths by using at least two interconnected meso-optical elements.

21 Claims, 2 Drawing Sheets

(56) References Cited

U.S. PATENT DOCUMENTS

| | | | |
|---|---|---|---|
| 5,796,112 A | 8/1998 | Ichie | |
| 2010/0265575 A1 | 10/2010 | Lippert et al. | |
| 2013/0214176 A1* | 8/2013 | Graves | G01N 15/1404 |
| | | | 250/459.1 |
| 2015/0070757 A1 | 3/2015 | Lippert et al. | |

FOREIGN PATENT DOCUMENTS

| | | |
|---|---|---|
| DE | 10 2010 046133 A1 | 3/2012 |
| EP | 0 627 643 A2 | 12/1994 |
| WO | 2009/080210 A2 | 7/2009 |

OTHER PUBLICATIONS

International Search Report and Written Opinion from Corresponding Application No. PCT/EP2015/062887; dated Aug. 5, 2015.
English Translation of International Search Report from Corresponding Application No. PCT/EP2015/062887; dated Aug. 5, 2015.

* cited by examiner

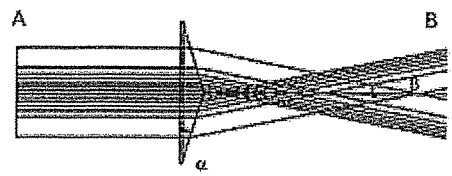
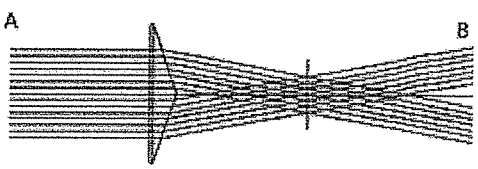
Fig. 1A          Fig. 1B
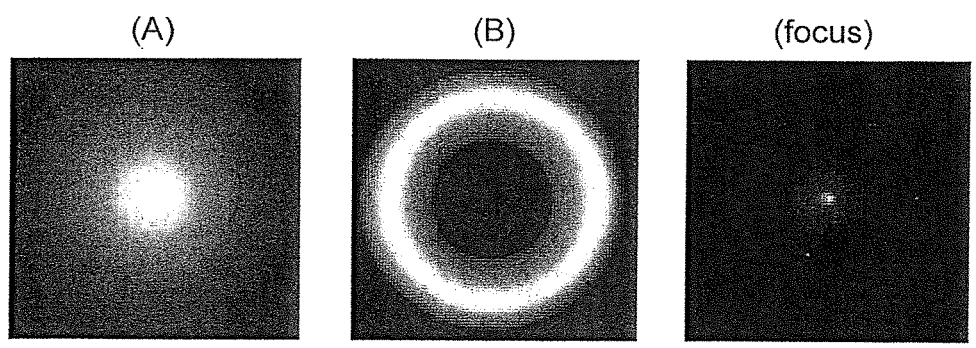
(A)          (B)          (focus)
Fig. 2A
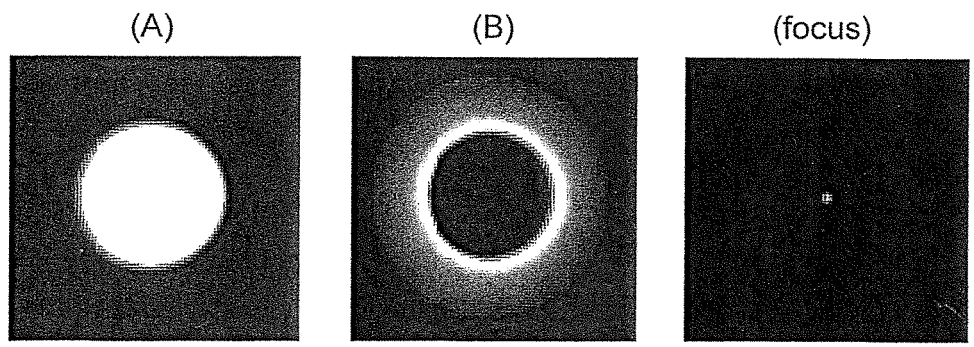
(A)          (B)          (focus)
Fig. 2B

LIGHT SHEET MICROSCOPY USING MESO-OPTICAL ELEMENTS

FIELD OF THE INVENTION

The present invention relates to devices and methods for generating light sheets and thin light beams with high Rayleigh lengths by using at least two interconnected meso-optical elements.

BACKGROUND OF THE INVENTION

Generating light beams or thin light sheets with high Rayleigh lengths is desired for various technical applications in which light beams with a transverse intensity profile as flat as possible over a large length of the light beam are useful. This includes in particular so-called light sheet microscopy, by means of which large-volume specimens can be analyzed three-dimensionally in layers. To this effect, the transparent fluorescent preparation is irradiated from the side with a thin light sheet, whereby an "optical section" is generated. The optical section results from the optical excitation of the fluorescence specifically in the plane of the light sheet. The section is recorded essentially perpendicular to the light sheet plane using a camera. The repetition enables a layered three-dimensional reconstruction of the specimen. A decisive factor for the resolution in the axial direction is the thickness of the light sheet. In the case of conventional Gaussian optics with essentially Gaussian distribution of the transverse intensity profile, the profile of the light sheet quickly becomes broader at increasing distance from the focus. Known alternatives thus use instead of Gaussian beams so-called Bessel beams that are generated with suitable alternative optical means in a manner known per se. Bessel beams have an intensive central intensity maximum. They however have undesirable secondary maxima in the form of coaxial "rings". These secondary maxima generate a disturbing background, which depending on the excitation behavior of the used fluorescence dye negatively widens the effective thickness of the analyzable optical layer.

Aside from this, the so-called "super-resolution" light microscopy according to the STED (stimulated emission depletion) principle was developed; it is described for example in DE 10 2009 008 646. In STED microscopy, the diffraction limitation of the excitation light is overcome in that a particular excitation light beam is provided which has a central excitation focus and is surrounded concentrically by a further light beam with a circular intensity profile of another wavelength, the so-called deexcitation light beam. Through the combination of a central excitation beam with this deexcitation beam encircling it, in connection with the excitation behavior of the fluorescence dye, the fluorescence emission in the specimen is reduced to a local area, which thereby lies below the diffraction limit of the excitation light itself. The disadvantage of the known optical configurations for generating the concentric STED illumination is the low Rayleigh length of the beams. In known configurations, the effective interaction of the two concentric light beams is thus possible only in one focus point in the beams' optical axis. It is desirable for the Rayleigh length of these concentric light beams to be increased. In particular, this should also make possible the combination of STED microscopy with light sheet microscopy.

Additionally, use of light sheet microscopy on the basis of Gaussian beams from lasers for two-photon excitation at wavelengths in the near-infrared range for irradiating barely transparent specimens thus is hardly practicable due then to the very small focus lengths.

BRIEF SUMMARY OF THE INVENTION

As solution of this technical problem, the invention provides an innovative optical system that is based on the use of several meso-optical elements, in particular Powell lenses or Axicon lenses (Axicons), and in particular in connection with a phase-shifting element, in particular an aspherical lens. The invention uses the insight that using a lens group with either at least two Power lenses or at least two Axicons and in particular one phase-shifting element, especially an aspherical lens, placed there between prevents the generation in the beam path of beam enlarging secondary maxima that notoriously arise when using only one meso-optical element. According to the invention, these secondary maxima eliminate each other through the use of two meso-optical elements in that the disturbing secondary maxima, as a result of a phase shift, can overlap destructively and thus be eliminated. The central beams overlap constructively, whereby ultimately a beam with high Rayleigh length is generated in the form of an elongated thin light sheet or of a thin central beam.

Accordingly, the invention is associated with a light sheet or a light beam that can be generated by using meso-optical elements, which is characterized in that the non-Gaussian beams generated by the meso-optical elements overlap in such a way that the disturbing secondary maxima disappear through interference and only the main maximum remains. Preferably, the light sheet is generated statically among others by using two Powell lenses as meso-optical elements. Alternatively, the light sheet is preferably generated (dynamically) among others by using two Axicons as meso-optical elements and optionally using a scan mirror for scanning the generated beam.

In an alternative variant, diffractive elements are used as meso-optical elements. A diffractive element is a so-called "spatial light modulator".

The invention also relates to a light sheet that is generated through overlapping of two inventively generated light sheets, wherein the one light sheet of these two light sheets has a longer wavelength and surrounds the other light sheet, which has a shorter wavelength. In doing so, the wavelengths of the two light sheets are preferably chosen in such as way that they represent excitation and deexcitation wavelengths that become effective as extremely thin light sheet in the fluorescent specimen in the context of STED microscopy.

Furthermore, it is possible to use the infrared irradiation of a two-photon laser (femtosecond laser) for generating the light sheet for the purpose of the two-photon excitation of fluorescence, in order to examine scattering or large specimens. Confocal line detection is preferably used to reduce the effect of the scattering of the emitted light. Alternatively, or additionally, a structured lighting is used in order to reduce the effect of the scattering of the emitted light.

The object of the invention is an optical configuration that is suitable for generating a light sheet or line beam containing at least a first group of lenses that, arranged in the beam direction along the optical axis, contains a first meso-optical element, followed by an aspherical lens and then by a second meso-optical element. In this context, the elements of the lens group are arranged according to the invention in such a way that they overlap the non-Gaussian beams generated by the meso-optical elements in such a way that the disturbing maxima disappear through interference and only the main maximum remains. In particular, the position and apex angle of the meso-optical elements are chosen such that constructive interference results in the area of the central light beam whilst the secondary maxima in contrast thereto eliminate each other through destructive interference. The beam first encounters the first meso-optical element, resulting in a non-diffraction-limited beam. This beam goes through the one aspherical lens, which generates an exactly calculated shift of the beam's amplitude and phase. The beam subsequently goes through a second meso-optical element, whereby due to destructive interference the secondary maxima (in particular ring structure) disappear and a central, especially hollow beam—when using Axicons as the first and second meso-optical elements—respectively a static light sheet—when using Powell lenses as the first and second meso-optical elements—will result.

Accordingly, a preferred object of the invention is an optical configuration, wherein the first and second meso-optical element in the lens group is respectively a Powell lens, whereby a static light sheet can be generated. An alternative preferred object of the invention is an optical configuration, wherein the first and second meso-optical element in the lens group is respectively an Axicon, whereby a light beam can be generated. This light beam is in particular a so-called "hollow beam" with a distinct circular ring-shaped intensity profile. In this configuration, it can be used, as will be described hereinafter in more detail, advantageously in the context of STED microscopy as excitation light beam and in particular as deexcitation light beam. Due to a very thin hollow beam being generated in the described optical configuration, it is ideal for super-resolution through the combination with STED. By means of STED, it is possible to break the diffraction limit in light microscopy in that for fluorescent specimens, the central excitation focus is surrounded by a desexcitation ring in an other wavelength, so that the focus is to a certain extent squeezed together and can be made smaller than the diffraction limit. This is admittedly also possible for a line, as described in DE 10 2009 008 646. In this case, the central excitation line is surrounded to a certain extent by a deexcitation tube. However, Gaussian beams for excitation and deexcitation are used with correspondingly lower Rayleigh length.

The non-classical beams described here according to the invention are outstandingly suitable for STED light sheet microscopy. Thus, according to the invention, it is also provided that in this way two beams with different wavelengths integrated within one another are generated simultaneously. The inner, extremely thin beam can be generated through a laser of the excitation wavelength. The hollow second beam overlapping this one can be generated through a laser of the deexcitation wavelength. Since according to the inventive configuration the two beams have great Rayleigh lengths, it is possible in this way to generate an extremely thin long coaxial beam. By actively scanning this beam, it is possible to achieve an extremely thin light sheet.

Alternatively, or additionally, the invention provides for a static light sheet to be generated in the form of a hollow light sheet in the optical configuration by using Powell lenses as first and second meso-optical element in the lens group. As in the case of a single beam, by overlapping the hollow light sheet of longer wavelength with a coaxial central static light sheet of shorter wavelength, it is possible to generate a combined light sheet that can be used in the context of STED. This represents a great improvement since the thickness of the (simple) light sheet so far constituted the factor limiting resolution in light sheet microscopy.

As described herein, in a preferred embodiment of the invention, at least one converging lens is connected downstream of the lens group and whose function it is to focus the light beam leaving the lens group to a line beam. In particular, if by using Axicons as first and second meso-optical element in the inventive optical configuration a central hollow beam is generated, the latter can hit in particular a plano-convex lens that focuses the beam to an extremely thin line. In a preferred variant of this embodiment, a scan mirror is additionally provided. By moving the scan mirror around a vertical axis, an extremely thin light sheet with a very high Rayleigh length is generated by shifting the line. A linear shifting of the line can in that case preferably be achieved either by moving the scan mirror correspondingly in radial as well as in X and Y directions. Alternatively, a converging lens is preferably provided in the beam direction before the scan mirror or a converging lens is provided downstream of the scan mirror.

A preferred embodiment of the invention is accordingly also an optical configuration wherein a scan mirror, suitable for the active beam diffraction and for dynamically generating a light sheet, is connected downstream of the inventive lens group. An object of the invention is thus also a method for generating a light sheet, wherein the method for generating a thin light beam is performed and the light beam is deflected with a scan mirror moving over it, so that the focused light beam when the scan mirror is moved scans an area and so that thus a light sheet is formed.

In a preferred embodiment, a light source is connected upstream of the inventive lens group in the beam direction and which is specifically designed for generating a light beam with flattened transverse intensity profile, a so-called "flat top" beam (FTB). Preferably, the light source comprises to this effect two aspherical lenses placed facing one another. In particular in the embodiment with a light sheet generated by scanning, a levelled flattened Gaussian laser beam (FGB) is first generated from an initially Gaussian laser beam with corresponding optical elements, for example two aspherical lenses.

An object of the invention is also a method for generating a thin light sheet or line beam, wherein a light beam is sent through the inventive optical configuration and wherein the elements of the inventive lens group are positioned in such a manner in their position along the optical axis of the light beam and if necessary the apex angle of the meso-optical elements in the inventive group is adapted in such a way that a phase shifting along the transverse enlargement of the light beam results, in such a way that the central beams overlap constructively and the secondary maxima eliminate each other through destructive interference, whereby a light beam or a light sheet is generated. This light beam or the light sheet has an exceptionally great Rayleigh length. In one variant of this method, it is additionally provided that from the generated thin light beam a light sheet is generated by active scanning, wherein the thin light beam previously generated is deflected with a moving scan mirror, so that the focused light beam when the scan mirror is moved scans an area and thus the light sheet is formed. This is an alternative to the previously described embodiment wherein, specifically by using Powell lenses as the first and second meso-optical elements of the inventive lens group, a so-called "static" light sheet is directly generated.

An object of the invention is also a method, wherein two overlapping light sheets of different wave length are formed, wherein the one light sheet of longer wavelength is hollow and surrounds the other light sheet of shorter wavelength. Preferably, the excitation and disexcitation wavelengths are chosen such that in the fluorescent specimen, an extremely thin light sheet becomes effective by means of STED (stimulated emission depletion).

Advantageously, the line beam generated by means of the inventive optical configuration is very thin, which means that the entire light energy (in particular laser energy) is concentrated on a very small cross section of approx. 1 µm diameter. Such small excitation cross sections advantageously allow femtosecond lasers to be used for the two-photo excitation of fluorescence in a specimen. The use of such lasers is advantageous for light sheet microscopy, since these emit light in the near-infrared range and the latter is less scattered in incompletely transparent specimens than visible light. The usability of two-photon lasers is known as such. Since however in the case of Gaussian beams the excitation cross section widens very strongly at increasing distance from the focus, the usable excitation line was only 400 µm in length. With the inventive solution, the excitation cross section barely increases at a distance from the focus, so that it is possible to achieve a long and very thin excitation line also with two-photon excitation. The line beam scanning described herein makes it possible to achieve a large thin so-called two-photon light sheet. This is advantageous in particular when using scattering or large transparent specimens. This system can preferably be further connected with confocal line detection in order to reduce the effect of scattering of the visible emitted light.

According to this invention, "confocal line detection" is understood to mean that light scattered with a mechanical or electronic slit aperture is blocked out sequentially prior to detection on the detector. The slit aperture is arranged optically conjugated with the excitation line. Instead of a slit aperture, structured lighting for suppressing stray light can also be used. Accordingly, the invention also provides for an optical configuration according to the invention that additionally has a slit aperture in particular controlled mechanically or electronically, arranged optically conjugated with the excitation line, in order to make it possible for scattered light to be sequentially blocked out prior to a detection. An object of the invention is thus a method wherein confocal line detection and/or structured lighting are used in order to reduce the effect of scattering of the emitted light.

An object of the invention is also a method wherein infrared irradiation of a femtosecond laser is used for two-photon excitation of fluorescence in the specimen, in particular for microscopically examining large and/or scattering specimens.

An object of the invention is also a method for microscopically examining large and/or scattering specimens, wherein a two-photon excitation of fluorescence in the specimen is generated by means of the inventive configuration.

An object of the invention is finally also the use of the inventive optical configuration disclosed herein for generating a thin light sheet respectively a light beam of high Rayleigh length.

BRIEF DESCRIPTION OF THE DRAWINGS

FIGS. 1A-1B show schematically the beam trajectory through a meso-optical element.
FIGS. 2A-2B show schematically the intensity distributions of the light beams.

DESCRIPTION OF EXAMPLE EMBODIMENTS

Figure 3:
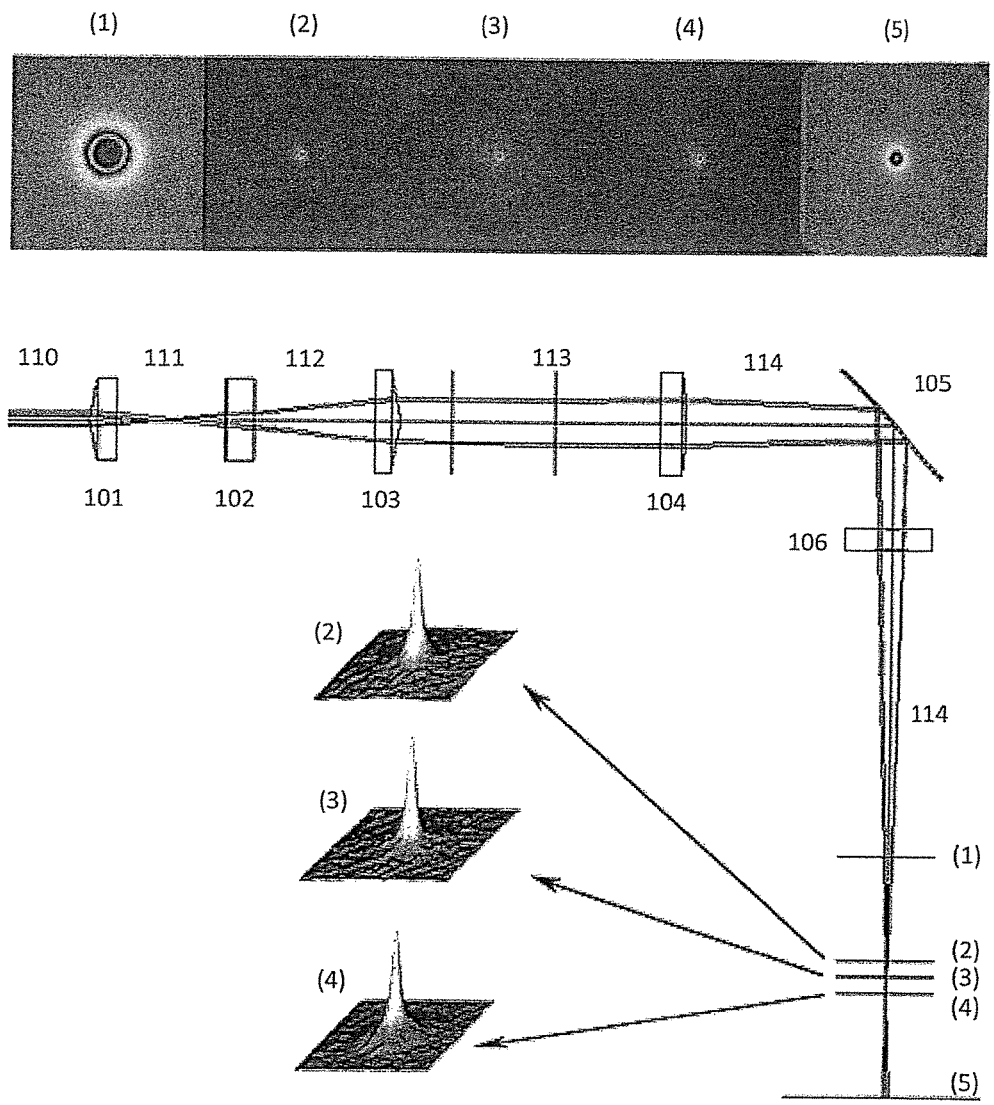
FIG. 3 shows a schematic representation of a light sheet generated through active scanning.

The invention will be described in more detail through the following embodiments.

FIG. 1 shows the beam trajectory and thus schematically sketches by means of the line thickness the transverse intensity profile when a light beam goes through a meso-optical element at point A, the focus point and at point B the transverse intensity profile is recorded. FIG. 1A shows a laser beam with transverse Gaussian profile (Gaussian beam) going through an Axicon lens. FIG. 1B shows a laser beam with transverse flattened Gaussian profile (FGB) going through an Axicon lens.

FIG. 2 shows schematically the intensity distributions of the light beams according to FIGS. 1A and 1B at the aperture of the Axicon lens (A) and at some distance from the focus (B) as well as at the focus point (focus) itself. FIG. 2A shows the intensity distribution of a Gaussian laser beam (FIG. 1A). FIG. 2B shows the corresponding intensity distributions of a flattened Gaussian laser beam (FIG. 1B).

FIG. 3 shows a schematic representation, not to scale, of a specific embodiment of the invention in connection with a light sheet generated through active scanning. A laser beam 110 first hits a first meso-optical element 101, in particular an Axicon, whereby a non-diffraction-limited beam 111 results. This beam goes through an aspherical lens as phase element 102, which generates an exactly calculated shift of the beam's amplitude and phase. The thus phase-corrected beam 112 subsequently goes through a second meso-optical element 103, whereby due to destructive interference the secondary maxima (ring structure) disappear and a central, especially hollow beam 113 will result. In the represented specific embodiment, this beam 113 then hits a plano-convex lens 104 and a scan mirror 105. The lens 104 focuses the beam to an extremely thin line 114. By moving the scan mirror 105 around an axis perpendicular to the drawing plane, an extremely thin light sheet with a very high Rayleigh length is generated by shifting the line. A linear shifting of the line 114 can in that case additionally be achieved either by moving the scan mirror 105 correspondingly in radial as well as in X and Y directions, or by placing the lens 104 drawn in front of the mirror 105 after the mirror or by additionally placing a lens 106 downstream of the mirror 105. For the sake of illustration, the transverse beam profiles in various planes of the focused beam 114 are represented by way of example: (1) 45 mm distance from the mirror, (2) 60 mm distance from the mirror, (3) 65 mm distance from the mirror, (4) 70 mm distance from the mirror, (5) 130 mm distance from the mirror.

The invention claimed:

1. Optical configuration, suitable for generating a light sheet or light beam, comprising a first lens group (100) which comprises, arranged in a beam direction along an optical axis:
   a first meso-optical element (101) and
   a second meso-optical element (103),
   wherein the first and second meso-optical element (101, 103) are arranged in such a way that non-Gaussian beams having main maximum and undesired secondary maxima generated by these elements overlap in such a way that the undesired secondary maxima cancel each other out and only the main maximum remains.

2. Optical configuration according to claim 1, suitable for generating a static light sheet, wherein each of the first and second meso-optical element (101, 103) is a Powell lens.

3. Optical configuration according to claim 2, wherein two overlapping light sheets of different wavelength can be formed, wherein the one light sheet of longer wavelength is hollow and surrounds the other light sheet of shorter wavelength.

4. Optical configuration according to claim 1, suitable for generating a light beam, wherein each of the first and second meso-optical element (101, 103) is an Axicon.

5. Optical configuration according claim 1, wherein in a group (100) between the first and second meso-optical element (101,103) a phase-shifting element (102) is provided.

6. Optical configuration according to claim 5, wherein the phase-shifting element (102) comprises an aspherical lens or consists thereof.

7. Optical configuration according to claim 1, wherein at least one converging lens (104, 106) for focusing the light beam to a line beam is provided downstream of the group (100).

8. Optical configuration according to claim 7, wherein a scan mirror (105), suitable for active beam deflection for generating a light sheet, is provided downstream of the group (100).

9. Optical configuration according to claim 1, wherein a light source, specifically designed for generating a light beam with flattened intensity profile, is provided upstream of the group (100).

10. Optical configuration according to claim 1, wherein the meso-optical elements are diffractive elements.

11. Method for generating a light sheet or line beam, wherein a light beam is sent through the optical configuration according to claim 1 and the elements of the group (100) are positioned in such a manner with respect to their position along the optical axis of the light beam and if necessary the apex angle of the meso-optical elements is adapted in such a way that a phase shift along an outer ring of the light beam results, in such a way that the central beams overlap constructively and the secondary maxima cancel each other out through destructive interference, so as to generate a light beam or a light sheet.

12. Method according to claim 11 for generating a static light sheet, wherein a Powell lens is used as meso-optical element.

13. Method according to claim 11 for generating a thin light beam, wherein an Axicon is used as meso-optical element.

14. Method for generating a light sheet, wherein the method according to claim 13 for generating a thin light beam is performed and the light beam is deflected with a scan mirror moving over it, so that the focused light beam when the scan mirror is moved scans a plane and so that thus a light sheet is formed.

15. Method according to claim 11, wherein two overlapping light sheets of different wave lengths are formed, wherein the one light sheet of longer wavelength is hollow and surrounds the other light sheet of shorter wavelength.

16. Method according to claim 15, wherein the excitation and deexcitation wavelengths are chosen such that in the fluorescent specimen, by means of STED (stimulated emission depletion) an extremely thin light sheet is effected.

17. Method according to claim 11, wherein infrared irradiation of a femtosecond laser is used for two-photon excitation of fluorescence in the specimen.

18. Method for microscopically examining large and/or scattering specimens, wherein the method according to claim 17 is performed for two-photon excitation of fluorescence in the specimen.

19. Method according to claim 11, wherein confocal line detection is used for reducing the effect of scattering of the emitted light.

20. Method according to claim 11, wherein structured lighting is used in order to reduce the effect of the scattering of the emitted light.

21. Use of the optical configuration according to claim 1 for generating a thin light sheet or a light beam, respectively, of high Rayleigh length.

* * * * *